(12) United States Patent
Angiolini et al.

(10) Patent No.: US 6,620,979 B2
(45) Date of Patent: Sep. 16, 2003

(54) HIGH PURITY 9,9-BIS-(HYDROXYPHENYL)-FLUORENE AND METHOD FOR THE PREPARATION AND PURIFICATION THEREOF

(75) Inventors: Simone Angiolini, Genova (IT); Mauro Avidano, Asti (IT)

(73) Assignee: Ferrania, S.p.A., Ferrania (IT)

( * ) Notice: Subject to any disclaimer, the term of this patent is extended or adjusted under 35 U.S.C. 154(b) by 0 days.

(21) Appl. No.: 10/118,573

(22) Filed: Apr. 8, 2002

(65) Prior Publication Data

US 2002/0188162 A1 Dec. 12, 2002

(30) Foreign Application Priority Data

Apr. 24, 2001 (IT) ..................... SV2001A0013

(51) Int. Cl.[7] .............................................. C07C 37/84
(52) U.S. Cl. ..................................................... 568/724
(58) Field of Search ......................................... 568/724

(56) References Cited

U.S. PATENT DOCUMENTS

| | | | |
|---|---|---|---|
| 4,024,194 A | 5/1977 | Corn, Jr. ..................... | 260/619 |
| 4,049,721 A | 9/1977 | Corn, Jr. et al. ............ | 260/619 |
| 4,387,209 A | 6/1983 | Rieder et al. ................ | 528/176 |
| 4,401,803 A | 8/1983 | Rieder ........................ | 528/176 |
| 4,430,493 A | 2/1984 | Rieder ........................ | 528/179 |
| 4,446,195 A | 5/1984 | Rieder et al. ................ | 428/458 |
| 4,467,122 A | 8/1984 | Szaboles ..................... | 568/727 |
| 4,675,458 A | 6/1987 | Riemann et al. ............. | 568/727 |
| 4,931,594 A | 6/1990 | Knebel et al. ............... | 568/727 |
| 5,110,994 A | 5/1992 | Fialla ......................... | 568/718 |
| 5,149,886 A | 9/1992 | Orth et al. ................... | 568/727 |
| 5,169,990 A | 12/1992 | Orth et al. ................... | 568/719 |
| 5,248,838 A | 9/1993 | Massirio et al. ............. | 568/727 |
| 5,304,688 A | 4/1994 | Bowman et al. ............. | 568/727 |

OTHER PUBLICATIONS

Abstract of JP–62–230741A (1986).
Abstract of JP–04–041450A (1990).
Abstract of JP–04–041451A (1990).
Abstract of JP–63–021836A (1986).
Abstract of JP–08–217713A (1995).
Abstract of JP–09–124530A (1995).

*Primary Examiner*—Michael L. Shippen
(74) *Attorney, Agent, or Firm*—Mark A. Litman & Assoc. P.A.

(57) ABSTRACT

A 9,9-bis (4-hydroxyphenyl) fluorene compound showing a melting curve maximum of at least 226.00° C. and a melting curve width at 5% equal to or lower than 1.30° C. A purification process for the preparation of 9,9-bis (4-hydroxyphenyl) fluorene compounds comprising a first purification step employing acetonitrile and a second purification step employing a solvent selected from the group consisting of aliphatic alcools, a mixture of aromatic hydrocarbons and aliphatic alco-hols and a mixture of aromatic hydrocarbons and nitrites. A synthesis method for the preparation of 9,9-bis (4-hydroxyphenyl) fluorene compounds comprising the steps of (a) reacting in an organic solvent a phenol compound with a 9-fluorenone in the presence of an acidic condensing agent, (b) separating the crude 9,9-bis (4-hydroxyphenyl) fluorene, and (c) purifying the crude 9,9-bis (4-hydroxyphenyl) fluorene, wherein the purifying method comprises a first purification step employing acetonitrile solvent and a second purification step employing a solvent selected from the group consisting of aliphatic alcools, a mixture of aromatic hydrocarbons and aliphatic alcohols and a mixture of aromatic hydrocarbons and nitrites.

13 Claims, 1 Drawing Sheet

HIGH PURITY 9,9-BIS-(HYDROXYPHENYL)-FLUORENE AND METHOD FOR THE PREPARATION AND PURIFICATION THEREOF

BACKGROUND OF THE INVENTION

1. Field of the Invention

The present invention relates to a novel high purity 9,9-bis (4-hydroxyphenyl) fluorene and to methods of preparation and purification thereof.

2. Background of the Art

In the modern polymeric manufacturing industry, bisphenols are used on a large scale in polycondensation reactions, particularly as monomers in the preparation of epoxy resins, polyurethanes, polycarbonates, polyethers and polyesters with especially high thermal resistance and good optical properties.

The compound 9,9-Bis-(4-HydroxyPhenyl) Fluorene and its substituted derivatives, generically known as BHPF, or Bisphenol F, is a useful monomer for the synthesis of the above mentioned polymers, particularly for the synthesis of polyesters, and especially for the preparation of polyarylates, i.e., polymers obtained from the copolymerization of BHPF with diacylic halides. These diacylic halide compounds show very high thermal resistance and exceptional optical properties ("High Performance Polyesters").

High performance polyesters, and particularly, aromatic polyesters, known as "polyarylates", have several important applications, such as:
1. polymeric films with mechanical properties higher than typical for a class of polymers, to be used in mechanical components where the resistance to a high number of stress-strain cycles (e.g., automotive components) is required;
2. replacement of glass, using films with very good optical properties, with good transparency to all the visible wavelength, low Yellow Index (e.g., as a components in liquid crystal—displays, ophthalmic lenses, goggle lenses, etc.);
3. thin films (under 10 $\mu$m) with good electrical insulation properties, especially at high temperatures (above 100° C.), e.g., for use with high performance electrical capacitors;
4. films suitable for the deposition of metal layers (e.g., copper, for the production of printed flexible circuits) or transparent conductive layers (e.g., ITO, Indium Tin Oxide).

These applications require polymeric materials with a very high glass transition temperature (Tg), for example above 300° C., a very high softening temperature and a very high melting temperature. A very high average molecular weight (AMW) (for example, above 500,000 Dalton), a narrow molecular weight distribution (MWD) and a low content of unreacted monomers or low molecular weight oligomers are other fundamental requirements desirable in high performance polyesters. These parameters are very important for the thermal and optical properties of these materials.

These results could be achieved previously only with the use of high purity reactants in the polymerization process, due to a well-known problem of polycondensation reactions (also known as a "step polymerization"). A description of this problem can be found in G. Odian, *Principles of Polymerization,* Chapter 2, "Step Polymerization", page 41, 3$^{rd}$ Ed., John Wiley & Sons, Inc. New York, 1991.

The successful synthesis of high molecular weight polycondensation polymers can be achieved only at very high conversion rates (generally higher than 99%, better higher than 99.5%), and this places several stringent requirements on the reaction conditions, such as a favorable equilibrium and the absence of side reactions.

This last requirement is strictly related to the above mentioned high purity of the reactants involved in the polymerization reaction, and the purity of the bisphenol(s) used in this reaction is one of the main issues in controlling the direction and existence of side reactions, because the presence, even in traces, of reactants or catalysts used in their synthesis, or the presence of reaction by-products can have a strong impact on the final result of the polymerization, often decreasing the molecular weight of the polymer. The separation of these by-products from the main product is of fondamental importance, because the different reactivities or functionalities of these by-products can have a heavy negative impact on the polymerization reactions, lowering the conversion degree of the reactants into the polymer and giving lower average molecular weight or introducing chain branching inside the structure of the final polymer. The separation process must be able to eliminate also the traces of reactants that can be present in the reaction product, because the most of them (phenols, acid catalysts) could react with e.g., the diacylic halides, breaking the polymerization reaction because of their monofunctionality or their different reactivity.

Several methods for the purification of BHPF are described in the art. The known methods are rather complex or involve large amounts of water or mixtures such as of water/organic solvents (e.g., alcohols, acetone or other carbonilic compounds), to eliminate from the product the residual catalysts (acids) or the excess of phenol used in the synthesis reaction. A great number of examples in literature also describe the use of halogenated solvents in the purification steps, such as methylene chloride, 1,2 dichloroethane, trichloroethylene and tetrachloroethane, which raise severe problems from the environmental and safety points of view.

U.S. Pat. No. 3,546,165 describes the synthesis of soluble, high melting, thermally stable linear polyesters. Example II describes the preparation of the 9,9-bis (4-hydroxyphenyl) fluorene by reaction of the reactants in molten phenol, precipitation with water and purification with toluene. The final product has a melting point of 224° C.

U.S. Pat. No. 4,024,194 describes a method for the purification of BHPF where the by-products, identified as 9-(4-hydroxyphenyl)-9-(2-hydroxyphenyl) fluorene (ortho-, para-isomer of BHPF) are eliminated using nitromethane ($CH_3NO_2$) as a solvent of crystallization. The final product has a melting point range of 224.8–225.4° C. and less than 0.5% of the aforesaid impurity.

U.S. Pat. No. 4,049,721 describes a method for purifying BHPF containing phenol as an impurity by using methanol and water and/or mixtures thereof.

U.S. Pat. Nos. 4,387,209, 4,401,803, 4,430,493, 4,446,195 and WO 92/03493 describe a process for the preparation of aromatic polyesters by using BHPF having a melting range of from 228° to 230° C. All patents make reference to U.S. Pat. No. 4,467,122 for the preparation of such BHPF by reaction of fluorenone in melted phenols in the presence of gaseous hydrogen halide and catalytic amounts of divalent, trivalent or tetravalent metal halides (where metal is selected from Ca, Fe, Ti, Sn and Al). The purification method includes washing with water and 1,2-dichloroethane to obtain a purity of 99.8% (determined by HPLC).

U.S. Pat. No. 4,675,458 describes a preparation method of BHPF by reacting fluorenone and phenol in presence of sulfuric acid having a concentration greater than 75% and mercaptans, as condensing agent. Methanol and isopropanol are used for purification, and the isolated product showed a melting point of 223° C.

U.S. Pat. No. 4,931,594 describes the synthesis of BHPF by reacting phenol and fluorenone in presence of an insoluble, strong acidic ion cationic exchange resin as a condensation catalyst, in a range of temperature between 20° C. to 150° C. The product was washed with acetone, water and isopropanol to give a final product showing a melting point between 221° C.–224° C.

U.S. Pat. No. 5,110,994 describes a method for the preparation of BHPF where the fluorenone is reacted in presence of an excess of phenol, hydrochloric acid and aluminum trichloride as catalyst, and the catalyst is dissolved in an anhydrous organic solvent. The raw product is treated with boiling water, acetone, and 1,2-dichloroethane. The final product has a DSC onset melting temperature of 225.5° C.

U.S. Pat. No. 5,149,886 describes a process for the synthesis of BHPF by condensing fluorenone and phenol in a molar ratio of 1:4 to 1:8 at 30 to 90° C. in the presence of gaseous hydrogen chloride and β-mercaptopropionic acid catalyst, where the improvement comprises distilling water of reaction and dissolved hydrochloridric acid from the complete reaction mixture, dissolving the distillation residue in a nitrile, separating the crystallized adduct of nitrile and BHPF from the nitrile and dissociating the adduct to recover BHPF. Acetonitrile, propionitrile, adipic acid dinitrile, fumaric acid dinitrile, glutaric acid dinitrile, and octanoic acid diitrile are disclosed as nitrites.

U.S. Pat. No. 5,169,990 discloses the synthesis of BHPF by condensation of fluorenone and phenol in a molar ratio of 1:4 to 1:8, in the presence of gaseous hydrogen chloride, and β-mercaptopropionic acid as catalyst where the completed reaction mixture is mixed with a polyalkylene glycol and then the excess of phenol is distilled from the mixture. Purity of 99.8% by HLC method is obtained with recrystalization in toluene/isopropanol or acetonitrile.

U.S. Pat. No. 5,248,838 describes a method for the synthesis of BHPF where the reactants are dissolved in an organic solvent (hydrocarbon solvents) and the BHPF is not soluble in this solvent at room temperature.

U.S. Pat. No. 5,304,688 describes the synthesis of BHPF in presence of a mercaptan cocatalyst and a solid superacid catalyst selected from the group consisting of metal sulfates, sulfated metal oxide, sulfated metal oxyhydroxides, sulfated metal oxysilicates, superacid metal oxides, and mixtures thereof.

JP Patent 62/230741 discloses a purification process for the production of high purity BHPF. The excess phenol present in the reaction media is removed and the crude product is dissolved in a solvent (diethyl ether, acetone, ethanol, propanol, dioxane or acetic acid) able to form an insoluble adduct with BHPF. This adduct is then separated (purity higher than 99%) and recrystallized from the above solvents or aromatic hydrocarbons to obtain further purified BHPF (purity higher than 99.6%).

JP Patent 04/041450 discloses a process for the synthesis of BHPF (or alkyl derivatives) by reacting phenol and fluorenone in presence of metal chloride and HCl or mercaptopropionic acid and HCl. An aliphatic alcohol is added to the reaction mixture to prepare a uniform solution. The BHPF is then precipitated adding water.

JP Patent 04/041451 discloses a process for the purification of colored bisphenols (for example, BHPF and its alkyl substituted derivatives). The crude product is dissolved in aliphatic ketone(s) and after its precipitation is recrystallizated with a mixed solvent of a lower aliphatic alcohol(s) (e.g., methanol, ethanol, n-propanol and isopropanol) and aromatic hydrocarbon(s) (e.g., benzene, toluene and xylene). The method allows colored bisphenols to be purified efficiently, providing colorless products.

JP Patent 63/021836 discloses a purification process for the BHPF where the crude product is first dissolved at room temperature in acetates and then added of a hydrocarbon-based solvent (e.g., hexane) to separate the crystal. The operation can be repeated, as necessary, and the product is finally dried at 100–150° C.

JP Patent 08/217713 discloses the use of hydrocarbon based solvents (without hydroxy functions and with a boiling point higher than phenol) as solvent media for the synthesis of BHPF. The unreacted phenol is removed by distillation. The distillation residue is then dissolved in an OH-free organic solvent, heated and cooled to precipitate BHPF.

JP Patent 09/124530 discloses a process for the synthesis of 9-fluorenone and its condensation with phenol in an inert solvent (aromatic hydrocarbon) in presence of acids and a mercaptocarboxylic acid. The BHPF obtained is suitable for the preparation of polyesters, polycarbonates or epoxy resins.

U.S. Pat. Nos. 4,618,699, 4,810,771, 4,904,755 describe a metod for the preparation of polyesters derived from BHPF and aromatic acids. No specific mention is made about the preparation and purification method of BHPF.

The prior art made clear that the purity of the BHPF is an essential condition for obtaining polyesters having superior properties. However, the purification processes described in literature are not able to give an "high purity BHPF" suitable for the use in large scale polycondensation reactions aimed to get polyesters for optical applications. In spite of the extensive prior art cited above, there is still the need of an improved technique for obtaining a extremely pure BHPF for preparation of polyester having superior optical and mechanical properties.

SUMMARY OF THE INVENTION

A 9,9-bis (4-hydroxyphenyl) fluorene compound showing a melting curve maximum of at least 226.00° C. and a melting curve width at 5% equal to or lower than 1.30° C.

A synthesis method for the preparation of 9,9-bis (4-hydroxyphenyl) fluorene compounds comprising the steps of (a) reacting in an organic solvent a phenol compound with a 9-fluorenone in the presence of an acidic condensing agent, (b) separating the crude 9,9-bis (4-hydroxyphenyl) fluorene, and (c) purifying the crude 9,9-bis (4-hydroxyphenyl) fluorene, characterized in that the purifying method comprises a first purification step employing acetonitrile solvent and a second purification step employing a solvent selected from the group consisting of aliphatic alcools, a mixture of aromatic hydrocarbons and aliphatic alcools and a mixture of aromatic hydrocarbons and nitrites.

A purification process for the preparation of 9,9-bis (4-hydroxyphenyl) fluorene compounds comprising a first purification step employing acetonitrile and a second purification step employing a solvent selected from the group consisting of aliphatic alcools, a mixture of aromatic hydrocarbons and aliphatic alcools and a mixture of aromatic hydrocarbons and nitrites.

DETAILED DESCRIPTION OF THE INVENTION

Figure 1:
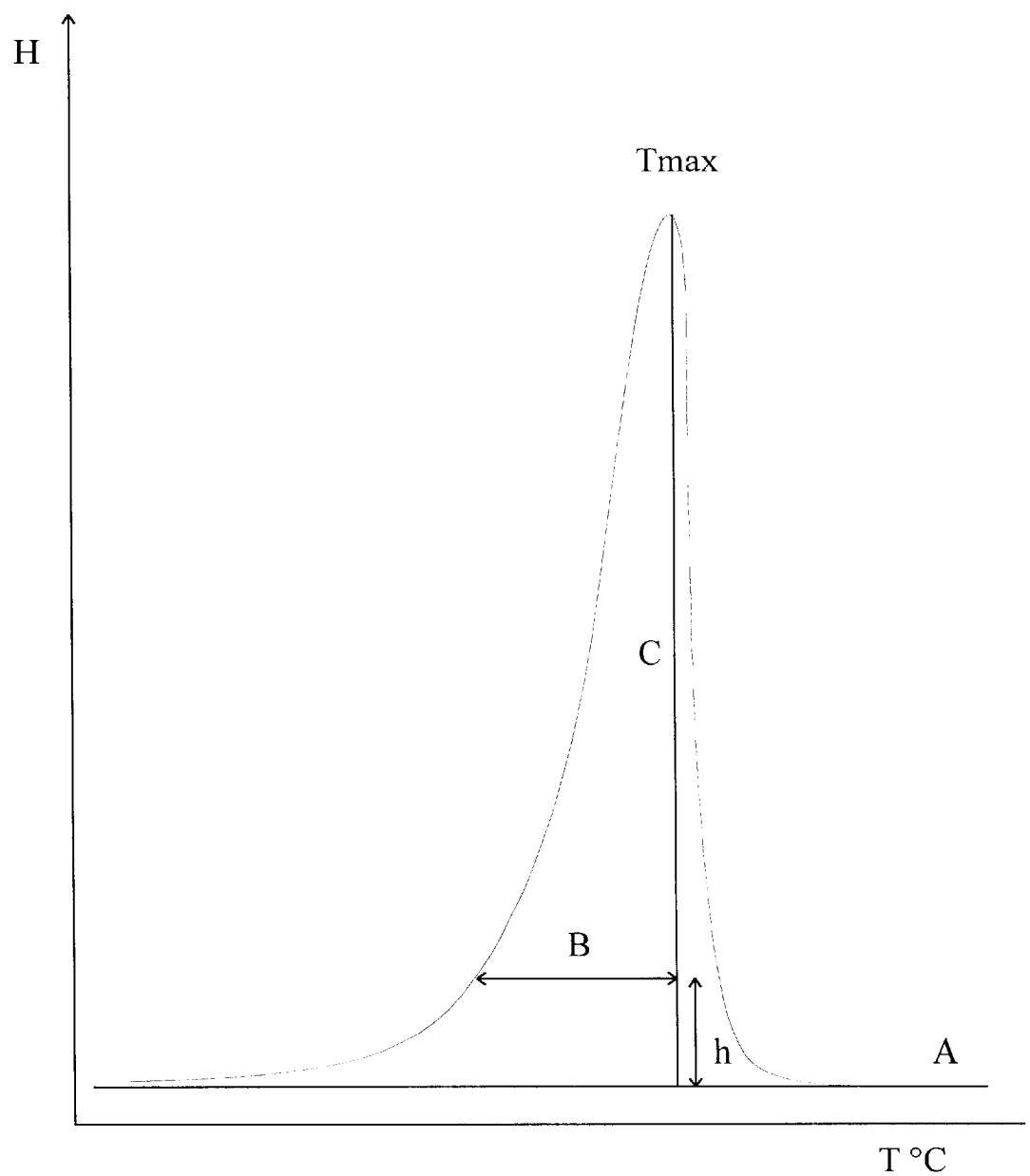
FIG. 1 is a graphic illustration of a differential scanning calorimetry (DSC) melting curve that illustrates the determination of the DSC parameters of the 9,9-bis (4-hydroxyphenyl) fluorene within the scope of the present invention.

The BHPF compound to be purified according to the method of the present invention may be synthetized according to any of the methods described in the art. The synthesis of the BHPF compound is preferably conducted by reacting in an organic solvent a phenol compound with a 9-fluorenone compound in the presence of an acidic condensing agent according to the method described in U.S. Pat. No. 5,248,838, herein incorporated for reference.

Useful phenol compounds include unsubstituted phenol and substituted phenols, provided that the substituent or substituents do not interfere with the condensation process. Useful substituents include by way of non-limiting examples alkyl groups, aryl groups, aralkyl groups, alkaryl groups, alkoxy groups, acyl groups, and halogen atoms. Preferred substituents include halogen atoms, preferably chloride and bromide, and alkyl groups containing from 1 to about 10 carbon atoms, more preferably, lower alkyl groups, such as those containing from 1 to about 5 carbon atoms, and most preferably, from 1 to 3 carbon atoms. The substituent or substituents are suitably located on the ortho and/or meta positions relative to the hydroxyl moiety. The para position relative to the hydroxyl moiety must remain free, because it is this position that participates in the condensation process. Preferably, one or both ortho positions are substituted, and more preferably both ortho positions are substituted. Non-limiting examples of suitable substituted phenols include o-cresol, m-cresol, o- or m-cumenol, 2,6-dimethylphenol, 2-methyl-6-ethylphenol, 2-chlorophenol, 2-bromophenol, 2,6-dibromophenol, 2,6-dichlorophenol, 2-methyl-6-bromophenol, 2-methyl-6-chlorophenol, 2,3,6-trimethylphenol, 2,3,5,6-tetramethylphenol, 2,6-di-t-butylphenol, o-phenylphenol, 2,6-diphenylphenol, 3,5-dimethylphenol, 3,5-diethylphenol, and o-benzylphenol.

Preferably, the phenol compound is the unsubstituted phenol or a phenol substituted at the ortho position(s) with a halogen atom and/or alkyl moiety of from 1 to about 5 carbon atoms. More preferably, the phenol compound is substituted at both the ortho positions with a halogen atom.

The 9-fluorenone compounds suitable for the synthesis of BHPF compounds includes unsubstituted 9-fluorenone and substituted 9-fluorenone, provided that the substituent or substituents do not interfere with the condensation process. Useful substituents include by way of non-limiting examples alkyl groups, aryl groups, aralkyl groups, alkaryl groups, alkoxy groups, acyl groups, and halogen atoms. Alkyl groups and halogen atoms are the preferred substituents for 9-fluorenone. Any position of the aryl rings of the 9-fluorenone can be substituted, preferably the 2- and 7-position. Preferred 9-fluorenone derivatives are 2,7-dibromo-9-fluorenone, 2,7-dimethyl-9-fluorenone, 2-bromo-7-methyl-9-fluorenone. However, the preferred compound is the unsubstituted 9-fluorenone.

Accordingly, the BHPF compound of the present invention include the unsubstituted 9,9-bis (4-hydroxyphenyl) fluorene and its substituted derivatives, and can be preferably represented by the following general formula:

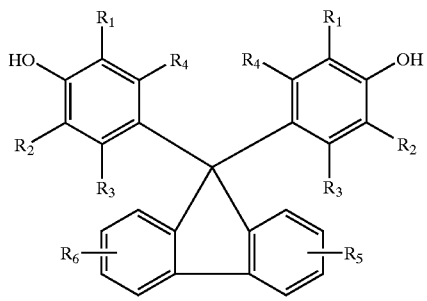

wherein R1 and R2 independently represent a hydrogen atom, a halogen atom, an alkyl group, an aryl group, an aralkyl group, an alkaryl group, an alkoxy group, and an acyl group; R3, R4, R5 and R6 independently represent a hydrogen atom, a halogen atom, an alkyl group, an aryl group, an aralkyl group, an alkaryl group, an alkoxy group, and an acyl group. Preferably, R1 and R2 independently represent a hydrogen atom, a halogen atom, more preferably chloride and bromide, and an alkyl group containing from 1 to about 10 carbon atoms, more preferably from 1 to 5 carbon atoms. Preferably, R3, R4, R5 and R6 independently represent a hydrogen atom, a halogen atom, more preferably chloride and bromide, and an alkyl group containing from 1 to about 10 carbon atoms, more preferably from 1 to 5 carbon atoms.

Any molar ratio of the phenol to 9-fluorenone is acceptable provided that a bis-hydroxy aromatic compound is formed as the predominant product in the process of this invention. Typically, the molar ratio of phenol to 9-fluorenone ranges from 2 to 6, more preferably from 2 to 4, and most preferably from 2 to 2.5. Below the lowest typical ratio of 2, by-product formation may increase. For example, the product bis-hydroxy aromatic compound may react at a free ortho position with excess ketone to yield higher condensation products. Above the highest typical ratio of 6, the separation and disposal of an excess of phenol may be expensive and problematical.

The organic solvents useful in the synthesis of BHPF compound are those that are good solvents or dispersants for the fluorenone and phenol compounds over a wide range of temperatures. That is, the organic solvent should maintain the fluorenone and phenol compounds in solution or dispersion at temperatures at least as high as the temperature at which the fluorenone and phenol compounds are reacted, and at least as low as the temperature to which the reaction mixture is cooled to facilitate precipitation or crystallization of the BHPF compound. The organic solvent also should not react with the fluorenone, phenol compound, acidic condensing agents or BHPF compound. Representative organic solvents include non-polar hydrocarbon solvents such as benzene, toluene, xylene, cyclohexane, hexane, heptane, nitromethane, halogenated hydrocarbons (e.g., trichloroethylene, 1,2-dichloroethane, methylene chloride and sym-tetrachloroethane) and mixtures thereof. For reasons of economy, toxicology, and availability, toluene is particularly useful as the organic solvent.

The acidic condensing agents employed in the synthsesis of BHPF compound are, for example, hydrogen chloride, sulfonic acids (as described in U.S. Pat. No. 5,248,838), sulfuric acid, divalent, trivalent or tetravalent halides (as described in U.S. Pat. No. 4,467,122), mercaptans and mercapto carboxylic acid (as described in U.S. Pat. No. 4,675,458), sulfonic acid type ion exchange resins or mixtures thereof. Any of the known means of combining the acidic condensing agent and the reaction mixture can be used. For example, gaseous hydrogen chloride may be bubbled through the reaction mixture over the course of the reaction. Alternatively, the acidic condensing agent or agents may be added to the reaction mixture at the beginning of the reaction. Also, the reaction mixture can be passed through a reactor filled with ion exchange resin. When more than one condensing agent is used, one condensing agent may be added to the reaction mixture at the beginning of the reaction and the other may be added slowly over the course of the reaction. In order to promote good mixing and a complete reaction, the reaction mixture should be continuously stirred once the acidic condensing agents are added.

The synthesis of BHPF product may be effected in a batch or a continuous type operation. For example, when a batch-type operation is used, the 9-fluorenone, the phenol compound and the organic solvent are placed in an appropriate apparatus such as a jacketed reaction kettle equipped with a stirring mechanism and agitated. After addition of the acidic condensing agent, the mixture is heated to the desired reaction temperature and maintained thereat for the duration of the reaction. Preferably, the reaction temperature is below 80° C., more preferably between 20 and 70° C. and most preferably between 40 and 60° C. Since the reaction mixture can be maintained in a readily stirrable condition throughout the reaction, it can also be more efficiently cooled. This is important because, if the reaction mixture cannot be cooled, the temperature of the reaction mixture may increase. One effect of a temperature increase (e.g., to a temperature greater than 80° C.) may be that more isomers, dimers and other impurities may form in the reaction mixture. At the end of the reaction, the reaction mixture is cooled to a temperature sufficiently low to effect precipitation or crystallization of the crude BHPF compound. Temperatures as low as ambient temperature (i.e., 25° C.) may be effective to cause precipitation, but preferably lower temperatures (e.g., below 20° C., or below 10° C., such as at 0° C.) are used. The crude BHPF compound is then recovered from the remaining reaction mixture by filtration or centrifugation and subjected to the purification process of the present invention.

The purification process of the present invention comprises a first purification step employing acetonitrile and a second purification step employing a solvent selected from the group consisting of aliphatic alcohols, a mixture of aromatic hydrocarbons and aliphatic alcohols and a mixture of aromatic hydrocarbons and nitrites.

In the first purification step, the crude BHPF is dispersed in acetonitrile in a container equipped with stirrer, reflux condenser and thermometer. The container can have any dimension and capacity depending on the production scale required. The dispersion is made at room temperature by employing from one to five liters of acetonitrile per kilogram of crude BHPF. The temperature of the dispersion is raised up to the reflux temperature of the acetonitrile solution (above about 80° C., more specifically, at or above about 81° C.), under stirring, obtaining a clear solution. The solution is then cooled at a temperature below 10° C., such as from 0 to 10° C., preferably from 0 to 5° C. and kept at this temperature for at least one hour, preferably for at least two hours to form a crystallization mixture.

The crystallization mixture is then filtered and the separated solid is washed with fresh solvent, and then dried at room temperature for at least one hour, preferably for at least two hours.

The obtained solid is then subjected to the second purification step with a solvent selected from the group consisting of aliphatic alcohols, a mixture of aromatic hydrocarbons and aliphatic alcohols and a mixture of aromatic hydrocarbons and nitrites.

The aliphatic alcohols useful in the process of the present invention include at least aliphatic alcohols having from 1 to 10 carbon atoms, preferably from 1 to 4 carbon atoms, such as, for example, methanol, ethanol, propanol, isopropanol, butanol, isobutanol, and t-butanol.

The aromatic hydrocarbons useful in the process of the present invention include at least benzene or substituted benzenes. Useful substituents are alkyl or alkenyl groups having from 1 to 5 carbon atoms. The preferred solvents are benzene, toluene, o-xilene, m-xilene, p-xilene, ethylbenzene, or styrene.

The nitrites useful in the process of the present invention include at least aliphatic nitrites and dinitriles, such as acetonitrile, proprionitrile, 3-methoxy-propionitrile, butyronitrile, malonodinitrile, adipodinitrile and valeronitrile, or aromatic nitrites and dinitriles, such as benzonitrile, naphthonitrile, phthalodinitrile.

The BHPF coming from the first purification step is redispersed in the selected solvent or solvent mixture in a container equipped with stirrer, reflux condenser and thermometer. The dispersion is made at room temperature by employing from one to five liters of solvent/solvent mixture per kilogram of BHPF. The dispersion is kept at room temperature or alternatively warmed up to the reflux temperature of the solvent/solvent mixture solution, under stirring, until obtaining a clear solution. The solution is then cooled at a temperature of less than about 10° C., for example from 0 to 10° C., preferably from 0 to 5° C. and kept at this temperature for at least one hour, preferably for at least two hours, and more preferably for at least four hours.

The resulting BHPF is separated and dried using conventionally known methods. The BHPF of the present invention is characterized by an extremely high grade of purity, never before reached with the conventional purification methods described in the art. When subjected to Differential Scanning Calorimetric (DSC) analysis, the BHPF obtained with the purification method of the present invention shows melting curve maximum of at least 226.00° C. and a melting curve width at 5% equal to or lower than 1.30° C. None of the methods described in the art were able to give such values.

Having reference to FIG. 1, the DSC parameters characterizing the present invention are the Tmax, expressed in Celsius degrees, and representing the temperature corresponding to the melting curve maximum of the sample under consideration and the melting curve width at 5%, expressed in Celsius degrees, representing the width (B) of the melting curve at 5% the height of the curve peak, measured between the line (C) perpendicular at the baseline (A) which crosses the maximum of the curve, and the side of the same melting curve at temperatures lower than the maximum of the curve.

The BHPF of the present invention is useful in polycondensation reactions for the production of polyurethanes, polycarbonates, polyethers, and polyesters having excellent mechanical, thermal and optical properties. The BHPF of the present invention is particularly useful for the preparation of polyesters, and more particularly for the preparation of polyarylates, obtained by reacting the BHPF with dicarboxylic acids or diacylic halides. Such polyarylates can be prepared with methods known in the art: there can be used for instance the solution polymerization method described in Ind. Eng. Chem. 51, 147, 1959, where a bifunctional carboxylic acid dihalide reacts with a bifunctional phenol (i.e., the BHPF) in an organic solution; the "molten" polymerization method, where a bifunctional carboxylic acid and a bifunctional phenol (i.e., the BHPF) are heated in the presence of acetic anhydride or diallylcarbonate, as described in JP patent application 38–26299; or the interfacial polymerization method, where a bifunctional carboxylic acid dihalide dissolved in a water-uncompatible organic solvent is mixed with a bifunctional phenol (i.e., the BHPF) dissolved in alkali water solution, as described in J. Polymer Science, XL399, 1959 and in EP patent applications 943,640 and 396,418.

The polyarylates obtained with the BHPF of the present invention show a higher average molecular weight and excellent mechanical, thermal and optical properties.

The present invention is now illustrated by reference to the following examples which however are not construed as limiting it.

EXAMPLES

Description of the Differential Scanning Calorimetric (DSC) Method

The DSC analysis has been made with a PERKIN ELMER DSC-4 Differential Scanning Calorimeter at a scan rate of 1.0° C./min with an aluminum pan PERKIN ELMER n° 0219-0041 and a sample weight of from 2.00 mg to 3.99 mg. The purge supply gas was nitrogen and the analysis temperature range was from 215° C. to 230° C. The calibration of the instrument was made with standard reference indium (atomic weight 114.82 a.u.) having an onset melting temperature of 156.60° C. and a DH melting of 28.45 J/g at the same scan rate of 1.0° C./min.

Having reference to FIG. 1, the DSC parameters characterizing the present invention are the Tmax, expressed in Celsius degrees, and representing the temperature corresponding to the melting curve maximum of the sample under consideration and the melting curve width at 5%, expressed in Celsius degrees, representing the width (B) of the melting curve at 5% the height of the curve peak, measured between the line (C) perpendicular at the baseline (A) which crosses the maximum of the curve, and the side of the same melting curve at temperatures lower than the maximum of the curve.

Preparation of the "crude BHPF"

In this example the "crude BHPF" is synthetized according Example 5 of U.S. Pat. No. 5,248,838. In a 500 ml four necked flask equipped with stirrer, reflux condenser and thermometer, 45.0 g (0.25 moles) of 9-fluorenone were charged together with 57.0 g of melted phenol (0.6 moles). 115 ml of toluene was added and the mixture was stirred to dissolve all the reactants. Then 0.22 ml (0.0025 moles) of 3-mercaptopropionic acid and 18.0 ml (0.28 moles) of methanesulfonic acid were charged in the flask. The methanesulfonic acid was dripped into the reaction solution in one hour. During the dripping the internal temperature increased to 40–42° C. in 30 min. (external cooling was necessary to limit the internal temperature at this value).

At the end of this exothermic step an external heating was provided in order to maintain 40° C. into the reaction vessel. The precipitation of the BHPF occurred after 90–120 min. The reaction was completed after 18 hours.

After cooling at room temperature in 1–2 hours, the product was then filtered and washed with fresh toluene (two washes with 50 ml each step). The product appeared like little (1–3 mm diameter) spheres with reddish brown color, with a weight loss of 10% at 90° C.

Example 1

Comparison

The crude BHPF was subjected to a single step purification process by employing acetonitrile solvent.

The crude BHPF was dispersed at room temperature with acetonitrile (2.5 l/kg of product) in a four necked flask equipped with stirrer, reflux condenser and thermometer, and warmed to the reflux temperature of the solvent, obtaining a clear, dark brown solution. This was then cooled to 0° C. and kept at this temperature for at least 2 hours. The crystallization mixture was then filtered on a vacuum funnel, washed with fresh solvent, kept in the vacuum funnel at room temperature for two hours, and dried in a vacuum oven (120° C.) for at least 16 hours. The product was analyzed with the DSC method described above, giving the results showed in Table 1.

Example 2

Invention

The crude BHPF was subjected to a double step purification process by employing acetonitrile solvent and a mixture of toluene: isopropanol (9:1 v/v).

The crude BHPF was dispersed at room temperature with acetonitrile (2.5 l/kg of product) in a four necked flask equipped with stirrer, reflux condenser and thermometer, and warmed to the reflux temperature of the solvent, obtaining a clear, dark brown solution. This was then cooled to 0° C. and kept at this temperature for at least 2 hours. The crystallization mixture was then filtered on a vacuum funnel, washed with fresh solvent, and then kept in the vacuum funnel at room temperature for two hours. The obtained solid was redispersed at room temperature with a mixture of toluene:isopropanol (9:1 v/v) (4 l/kg of product), warmed to the reflux temperature of the solvent mixture, obtaining a clear, pale yellow solution. This was then cooled to 0°/–5C and kept at this temperature for at least 4 hours. The crystallization mixture was then filtered on a vacuum funnel, washed with fresh solvent, kept in the vacuum funnel at room temperature for two hours, and dried in a vacuum oven (120° C.) for at least 16 hours The product, after complete drying, was analyzed with the DSC method described above, giving the results showed in Table 1.

Example 3

Invention

The crude BHPF was subjected to a double step purification process by employing acetonitrile and a mixture of toluene:acetonitrile.

The crude BHPF was dispersed at room temperature with acetonitrile (2.5 l/kg of product) in a four necked flask equipped with stirrer, reflux condenser and thermometer, and warmed to the reflux temperature of the solvent, obtaining a clear, dark brown solution. This was then cooled to 0° C. and kept at this temperature for at least 2 hours. The crystallization mixture was then filtered on a vacuum funnel, washed with fresh solvent, and then kept in the vacuum funnel at room temperature for two hours. The obtained solid was redispersed at room temperature with a mixture of toluene:acetonitrile (9.3:0.7 v/v) (5.5 l/kg of product), warmed to the reflux temperature of the solvent mixture, obtaining a clear, pale yellow solution. This was then cooled to 0°/–5C and kept at this temperature for at least 4 hours. The crystallization mixture was then filtered on a vacuum funnel, washed with fresh solvent, kept in the vacuum funnel at room temperature for two hours, and dried in a vacuum oven (120° C.) for at least 16 hours.

The product was analyzed with the DSC method described above, giving the results showed in Table 1.

Example 4

Invention

The crude BHPF was subjected to a double step purification process by employing acetonitrile and isopropanol.

The crude BHPF was dispersed at room temperature with acetonitrile (2.5 l/kg of product) in a four necked flask equipped with stirrer, reflux condenser and thermometer, and warmed to the reflux temperature of the solvent, obtaining a clear, dark brown solution. This was then cooled to 0° C. and kept at this temperature for at least 2 hours. The crystallization mixture was then filtered on a vacuum funnel, washed with fresh solvent, and then kept in the vacuum funnel at room temperature for two hours. The obtained solid was redispersed at room temperature with isopropanol (3.0 l/kg of product), stirred for at least two hours, and then cooled to 0° and kept at this temperature for at least 4 hours. The crystallization mixture was then filtered on a vacuum funnel, washed with fresh solvent, kept in the vacuum funnel at room temperature for two hours, and dried in a vacuum oven (90° C.) for at least 16 hours.

The product was analyzed with the DSC method described above, giving the results showed in Table 1.

Example 5

Comparison

The crude BHPF was subjected to a single step purification process by employing acetone.

The crude BHPF was dispersed at room temperature with acetone (4.0 l/kg of product) in a four necked flask equipped with stirrer, reflux condenser and thermometer, and warmed to the reflux temperature of the solvent, obtaining a clear, dark brown solution. This was then cooled to 0C and kept at this temperature for at least 2 hours. The crystallization mixture was then filtered on a vacuum funnel, washed with fresh solvent, kept in the vacuum funnel at room temperature for two hours, and dried in a vacuum oven (90° C.) for at least 16 hours.

The product was analyzed with the DSC method described above, giving the results showed in Table 1.

Example 6

Comparison

The crude BHPF was subjected to a double step purification process by employing acetone and a mixture of toluene: isopropanol (9:1 v/v).

The crude BHPF was dispersed at room temperature with acetone (4.0 l/kg of product) in a four necked flask equipped with stirrer, reflux condenser and thermometer, and warmed to the reflux temperature of the solvent, obtaining a clear, dark brown solution. This was then cooled to 0° C. and kept at this temperature for at least 2 hours. The crystallization mixture was then filtered on a vacuum funnel, washed with fresh solvent, and then kept in the vacuum funnel at room temperature for two hours. The obtained solid was redispersed at room temperature with a mixture of toluene:isopropanol (9:1 v/v) (4.3 l/kg of product), warmed to the reflux temperature of the solvent mixture, obtaining a clear, pale yellow solution. This was then cooled to 0° and kept at this temperature for at least 4 hours. The crystallization mixture was then filtered on a vacuum funnel, washed with fresh solvent, kept in the vacuum funnel at room temperature for two hours, and dried in a vacuum oven (120° C.) for at least 16 hours.

The product was analyzed with the DSC method described above, giving the results showed in Table 1.

Example 7

Comparison

The crude BHPF was subjected to a double step purification process by employing acetone and dioxane.

The crude BHPF was dispersed at room temperature with acetone (4.0 l/kg of product) in a four necked flask equipped with stirrer, reflux condenser and thermometer, and warmed to the reflux temperature of the solvent, obtaining a clear, dark brown solution. This was then cooled to 0° C. and kept at this temperature for at least 2 hours. The crystallization mixture was then filtered on a vacuum funnel, washed with fresh solvent, and then kept in the vacuum funnel at room temperature for two hours. The obtained solid was redispersed at room temperature with dioxane (3.15 l/kg of product), stirred for at least two hours, and then cooled to 0° and kept at this temperature for at least 4 hours. The crystallization mixture was then filtered on a vacuum funnel, washed with fresh solvent, kept in the vacuum funnel at room temperature for two hours, and dried in a vacuum oven (90° C.) for at least 16 hours.

The product was analyzed with the DSC method described above, giving the results showed in Table 1.

Example 8

Comparison

The crude BHPF was subjected to a double step purification process by employing acetone and isopropanol.

The crude BHPF was dispersed at room temperature with acetone (4.0 l/kg of product) in a four necked flask equipped with stirrer, reflux condenser and thermometer, and warmed to the reflux temperature of the solvent, obtaining a clear, dark brown solution. This was then cooled to 0° C. and kept at this temperature for at least 2 hours. The crystallization mixture was then filtered on a vacuum funnel, washed with fresh solvent, and then kept in the vacuum funnel at room temperature for two hours. The obtained solid was redispersed at room temperature with isopropanol (2.0 l/kg of product), stirred for at least two hours, and then cooled to 0° and kept at this temperature for at least 4 hours. The crystallization mixture was then filtered on a vacuum funnel, washed with fresh solvent, kept in the vacuum funnel at room temperature for two hours, and dried in a vacuum oven (90° C.) for at least 16 hours.

The product was analyzed with the DSC method described above, giving the results showed in Table 1.

Example 9

Comparison

The crude BHPF was subjected to a double step purification process by employing acetone and ethanol.

The crude BHPF was dispersed at room temperature with acetone (4.0 l/kg of product) in a four necked flask equipped with stirrer, reflux condenser and thermometer, and warmed to the reflux temperature of the solvent, obtaining a clear, dark brown solution. This was then cooled to 0° C. and kept at this temperature for at least 2 hours. The crystallization mixture was then filtered on a vacuum funnel, washed with fresh solvent, and then kept in the vacuum funnel at room temperature for two hours. The obtained solid was redispersed at room temperature with ethanol (3.0 l/kg of product), warmed to the reflux temperature of the solvent, obtaining a clear, yellow solution. This was then cooled to 0° and kept at this temperature for at least 2 hours. The crystallization mixture was then filtered on a vacuum funnel, washed with fresh solvent, kept in the vacuum funnel at room temperature for two hours, and dried in a vacuum oven (90° C.) for at least 16 hours.

The product was analyzed with the DSC method described above, giving the results showed in Table 1.

Example 10

Comparison

The crude BHPF was subjected to a double step purification process by employing acetone and methanol.

The crude BHPF was dispersed at room temperature with acetone (4.0 l/kg of product) in a four necked flask equipped with stirrer, reflux condenser and thermometer, and warmed to the reflux temperature of the solvent, obtaining a clear, dark brown solution. This was then cooled to 0° C. and kept at this temperature for at least 2 hours. The crystallization mixture was then filtered on a vacuum funnel, washed with fresh solvent, and then kept in the vacuum funnel at room temperature for two hours. The obtained solid was redispersed at room temperature with methanol (1.65 l/kg of product), stirred for at least two hours, and then cooled to 0° and kept at this temperature for at least 4 hours. The crystallization mixture was then filtered on a vacuum funnel, washed with fresh solvent, kept in the vacuum funnel at

Example 11

Comparison

The crude BHPF was subjected to a single step purification process by employing ethanol.

The crude BHPF was dispersed at room temperature with ethanol (2.7 l/kg of product) in a four necked flask equipped with stirrer, reflux condenser and thermometer, and warmed to the reflux temperature of the solvent, obtaining a clear, dark brown solution. This was then cooled to 0° C. and kept at this temperature for at least 2 hours. The crystallization mixture was then filtered on a vacuum funnel, washed with fresh solvent, kept in the vacuum funnel at room temperature for two hours, and dried in a vacuum oven (90° C.) for at least 16 hours.

The product was analyzed with the DSC method described above, giving the results showed in Table 1.

Example 12

Comparison

The crude BHPF was subjected to a double step purification process by employing ethanol and acetone.

The crude BHPF was dispersed at room temperature with ethanol (2.7 l/kg of product) in a four necked flask equipped with stirrer, reflux condenser and thermometer, and warmed to the reflux temperature of the solvent, obtaining a clear, dark brown solution. This was then cooled to 0° C. and kept at this temperature for at least 2 hours. The crystallization mixture was then filtered on a vacuum funnel, washed with fresh solvent, and then kept in the vacuum funnel at room temperature for two hours. The obtained solid was redispersed at room temperature with acetone (3.4 l/kg of product), warmed to the reflux temperature of the solvent, obtaining a clear, pale yellow solution. This was then cooled to 0° and kept at this temperature for at least 2 hours. The crystallization mixture was then filtered on a vacuum funnel, washed with fresh solvent, kept in the vacuum funnel at room temperature for two hours, and dried in a vacuum oven (90° C.) for at least 16 hours.

The product was analyzed with the DSC method described above, giving the results showed in Table 1.

Example 13

Comparison

The crude BHPF was subjected to a double step purification process by employing twice isopropanol.

The crude BHPF was dispersed at room temperature with isopropanol (2.25 l/kg of product) in a four necked flask equipped with stirrer, reflux condenser and thermometer, and warmed to the reflux temperature of the solvent, obtaining a clear, dark brown solution. This was then cooled to 0° C. and kept at this temperature for at least 2 hours. The crystallization mixture was then filtered on a vacuum funnel, washed with fresh solvent, and then kept in the vacuum funnel at room temperature for two hours. The obtained solid was redispersed at room temperature with isopropanol (2.5 l/kg of product), stirred for at least two hours, and then cooled to 0° and kept at this temperature for at least 4 hours. The crystallization mixture was then filtered on a vacuum funnel, washed with fresh solvent, kept in the vacuum funnel at room temperature for two hours, and dried in a vacuum oven (90° C.) for at least 16 hours.

The product was analyzed with the DSC method described above, giving the results showed in Table 1.

Example 14

Comparison

The crude BHPF was subjected to a double step purification process by employing isopropanol and acetone.

The crude BHPF was dispersed at room temperature with isopropanol (2.25 l/kg of product) in a four necked flask equipped with stirrer, reflux condenser and thermometer, and warmed to the reflux temperature of the solvent, obtaining a clear, dark brown solution. This was then cooled to 0° C. and kept at this temperature for at least 2 hours. The crystallization mixture was then filtered on a vacuum funnel, washed with fresh solvent, and then kept in the vacuum funnel at room temperature for two hours. The obtained solid was redispersed at room temperature with acetone (3.0 l/kg of product), warmed to the reflux temperature of the solvent, obtaining a clear, pale yellow solution. This was then cooled to 0° and kept at this temperature for at least 2 hours. The crystallization mixture was then filtered on a vacuum funnel, washed with fresh solvent, kept in the vacuum funnel at room temperature for two hours, and dried in a vacuum oven (90° C.) for at least 16 hours.

The product was analyzed with the DSC method described above, giving the results showed in Table 1.

Example 15

Comparison

The crude BHPF was subjected to a double step purification process by employing twice a mixture of toluene:isopropanol (9:1 v/v).

The crude BHPF was dispersed at room temperature with a mixture of toluene:isopropanol (9:1 v/v) (3.8 l/kg of product) in a four necked flask equipped with stirrer, reflux condenser and thermometer, and warmed to the reflux temperature of the solvent, obtaining a clear, dark brown solution. This was then cooled to 0° C. and kept at this temperature for at least 2 hours. The crystallization mixture was then filtered on a vacuum funnel, washed with fresh toluene, and then kept in the vacuum funnel at room temperature for two hours. The obtained solid was redispersed at room temperature with a mixture of toluene:isopropanol (9:1 v/v) (1.5 l/kg of product), warmed to the reflux temperature of the solvent, obtaining a clear, yellow solution. This was then cooled to 0° and kept at this temperature for at least 2 hours. The crystallization mixture was then filtered on a vacuum funnel, washed with fresh toluene, kept in the vacuum funnel at room temperature for two hours, and dried in a vacuum oven (90° C.) for at least 16 hours.

The product was not analyzed with the DSC method due to its degradation.

Example 16

Comparison

The crude BHPF was subjected to a double step purification process by employing twice a mixture of toluene:acetonitrile (9.3:0.7 v/v).

The crude BHPF was dispersed at room temperature with a mixture of toluene: acetonitrile (9.3:0.7 v/v) (5.5 l/kg of product) in a four necked flask equipped with stirrer, reflux condenser and thermometer, and warmed to the reflux temperature of the solvent, obtaining a clear, dark brown solution. This was then cooled to 0° C. and kept at this temperature for at least 2 hours. The crystallization mixture was then filtered on a vacuum funnel, washed with fresh toluene, and then kept in the vacuum funnel at room temperature for two hours. The obtained solid was redispersed at room temperature with a mixture of toluene:acetonitrile (9.3:0.7 v/v) (3.7 l/kg of product), warmed to the reflux temperature of the solvent, obtaining a clear, pale brown solution. This was then cooled to 0° and kept at this temperature for at least 2 hours. The crystallization mixture was then filtered on a vacuum funnel, washed with fresh toluene, kept in the vacuum funnel at room temperature for two hours, and dried in a vacuum oven (90° C.) for at least 16 hours.

The product was not analyzed with the DSC method due to its degradation.

TABLE 1

| Example | Solvent 1 | Solvent 2 | Tmax ° C. | Width at 5% ° C. |
|---|---|---|---|---|
| 1 (C) | Acetonitrile | — | 226.37 | 1.95 |
| 2 (I) | Acetonitrile | Toluene: Isopropanol (9:1 v/v) | 226.41 | 1.02 |
| 3 (I) | Acetonitrile | Toluene: Acetonitrile (9.3:0.7 v/v) | 226.70 | 0.83 |
| 4 (I) | Acetonitrile | Isopropanol | 226.66 | 1.26 |
| 5 (C) | Acetone | — | 226.41 | 2.34 |
| 6 (C) | Acetone | Toluene: Isopropanol (9:1 v/v) | 226.19 | 1.80 |
| 7 (C) | Acetone | Dioxane | 226.46 | 1.71 |
| 8 (C) | Acetone | Isopropanol | 226.09 | 1.51 |
| 9 (C) | Acetone | Ethanol | 226.08 | 1.61 |
| 10 (C) | Acetone | Methanol | 226.33 | 1.71 |
| 11 (C) | Ethanol | — | 222.89 | 3.57 |
| 12 (C) | Ethanol | Acetone | 225.73 | 2.72 |
| 13 (C) | Isopropanol | Isopropanol | 221.76 | 5.09 |
| 14 (C) | Isopropanol | Acetone | 225.08 | 2.47 |
| 15 (C) | Toluene: Isopropanol (9:1 v/v) | Toluene: Isopropanol (9:1 v/v) | Degraded | Degraded |
| 16 (C) | Toluene: Acetonitrile (9.3:0.7 v/v) | Toluene: Acetonitrile (9.3:0.7 v/v) | Degraded | Degraded |

Preparation of Polyarylate Film

Polymer 1 was obtained by taking the purified BHPF compound of example 1 and polymerizing it with the interfacial polycondensation technique as described in EP Patent 396,418, utilizing a mixture of 50 mole-% of terephthalic and isophthalic acids. Film 1 was obtained by solvent casting using a 10% weight methylene chloride solution of the polymer 1. Film 1 was then dried for 3 hours at a temperature of 25° C., gradually increasing the temperature up to a maximum of 160° C.

Polymers 2 to 16 and Films 2 to 16 were obtained by the same procedure, but using the purified BHPF compounds of examples 2–16, respectively.

The Gel Permeation Chromatography (GPC) data relative to the polymers 1 to 16 are reported in Table 2. The data of Table 2 clearly show that a polymer with higher molecular weight was obtained by using the purified BHPF compounds of the present invention.

TABLE 2

| Polymer | Mw | Mn |
|---|---|---|
| 1 (C) | 308,000 | 72,000 |
| 2 (I) | 679,000 | 101,000 |
| 3 (I) | 705,000 | 79,000 |
| 4 (I) | 720,000 | 85,000 |
| 5 (C) | 290,000 | 72,000 |
| 6 (C) | 244,000 | 63,000 |
| 7 (C) | N.A. | N.A. |
| 8 (C) | 402,000 | 83,000 |
| 9 (C) | N.A. | N.A. |
| 10 (C) | 379,000 | 82,000 |
| 11 (C) | N.A. | N.A. |

TABLE 2-continued

| Polymer | Mw | Mn |
|---|---|---|
| 12 (C) | N.A. | N.A. |
| 13 (C) | 329,000 | 78,000 |
| 14 (C) | N.A. | N.A. |
| 15 (C) | Degraded | Degraded |
| 16 (C) | Degraded | Degraded |

What is claimed is:

1. A purification process for the preparation of 9,9-bis(4-hydroxyphenyl) fluorene compounds, said process comprising purifying an impure 9,9-bis(4-hydroxyphenyl) fluorene compound by at least two purification steps, a first purification step employing acetonitrile solvent and a second purification step employing a solvent selected from the group consisting of aliphatic alcools, a mixture of aromatic hydrocarbons and aliphatic alcohols and a mixture of aromatic hydrocarbons and nitrites.

2. The purification process of claim 1, characterized in that said aliphatic alcohol is selected from the group consisting of methanol, ethanol, propanol, isopropanol, butanol, isobutanol, t-butanol, and n-pentanol.

3. The purification process of claim 1, characterized in that said aromatic hydrocarbon is selected from the group consisting of benzene, toluene, o-xylene, m-xylene, p-xylene, ethylbenzene, and styrene.

4. The purification process of claim 1, characterized in that said nitrile is selected from the group consisting of acetonitrile, proprionitrile, 3-methoxy-propionitrile, butyronitrile, malonodinitrile, adipodinitrile, valeronitrile, benzonitrile, naphthonitrile and phthalodinitrile.

5. A synthesis method for the preparation of 9,9-bis(4-hydroxyphenyl) fluorene compounds comprising the steps of (a) reacting in an organic solvent a phenol compound with a 9-fluorenone compound in the presence of an acidic condensing agent, (b) separating crude 9,9-bis(4-hydroxyphenyl) fluorene compound, and (c) purifying the crude 9,9-bis (4-hydroxyphenyl) fluorene compound, by a purifying method comprising a first purification step employing acetonitrile solvent and a second purification step employing a solvent selected from the group consisting of a) aliphatic alcohols, b) a mixture of aromatic hydrocarbons and aliphatic alcohols and c) a mixture of aromatic hydrocarbons and nitrites.

6. The synthesis method of claim 5, characterized in that said aliphatic alcohol is selected from the group consisting of methanol, ethanol, propanol, isopropanol, butanol, isobutanol, t-butanol, and n-pentanol.

7. The synthesis method of claim 5, characterized in that said aromatic hydrocarbon is selected from the group consisting of benzene, toluene, o-xylene, m-xylene, p-xylene, ethylbenzene, and styrene.

8. The synthesis method of claim 5, characterized in that said nitrile is selected from the group consisting of acetonitrile, proprionitrile, 3-methoxy-propionitrile, butyronitrile, and valeronitrile, and benzonitrile.

9. A 9,9-bis (4-hydroxyphenyl) fluorene compound showing a melting curve maximum of at least 226.00° C. and a melting curve width at 5% equal to or lower than 1.30° C.

10. A 9,9-bis (4-hydroxyphenyl) fluorene compound showing a melting curve maximum of at least 226.00° C. and a melting curve width at 5% equal to or lower than 1.10° C.

11. The purification process of claim 1 wherein the first purification step comprises recrystallization from the acetonitrile solvent.

12. The purification process of claim 1 wherein the second purification step comprises recrystallization from a solvent system comprising a solvent system selected from the group consisting of a) aliphatic alcohols, b) a mixture of aromatic hydrocarbons and aliphatic alcohols and c) a mixture of aromatic hydrocarbons and nitrites.

13. The purification process of claim 11 wherein the second purification step comprises recrystallization from a solvent system comprising a solvent system selected from the group consisting of a) aliphatic alcohols, b) a mixture of aromatic hydrocarbons and aliphatic alcohols and c) a mixture of aromatic hydrocarbons and nitrites.

* * * * *